United States Patent
Ovadia et al.

(10) Patent No.: US 6,949,763 B2
(45) Date of Patent: Sep. 27, 2005

(54) SEMICONDUCTOR AND NON-SEMICONDUCTOR NON-DIFFUSION-GOVERNED BIOELECTRODES

(76) Inventors: Marc Ovadia, 3240 N. Lake Shore Dr., Chicago, IL (US) 60657; Jeanne E. Pemberton, 1306 E. University Blvd., Tucson, AZ (US) 85721

(*) Notice: Subject to any disclaimer, the term of this patent is extended or adjusted under 35 U.S.C. 154(b) by 0 days.

(21) Appl. No.: 10/261,000

(22) Filed: Sep. 30, 2002

(65) Prior Publication Data

US 2003/0114904 A1 Jun. 19, 2003

Related U.S. Application Data

(60) Provisional application No. 60/328,773, filed on Oct. 11, 2001.

(51) Int. Cl.[7] .................... H01L 51/00; H01L 35/24; A61N 1/00; A61N 1/05; A61N 1/04
(52) U.S. Cl. .................... 257/40; 257/57; 257/72; 257/347; 607/116; 607/115; 607/127; 607/59; 607/121; 607/53; 607/54; 600/345; 600/300; 600/309; 600/347; 600/365; 600/377; 600/393
(58) Field of Search .................... 600/345–350, 600/309, 300, 365, 381, 393, 348; 438/238–513; 607/116–122, 53, 129, 115, 127, 59; 257/40, 57, 72, 347; 60/27, 157

(56) References Cited

U.S. PATENT DOCUMENTS

| | | | |
|---|---|---|---|
| 4,352,360 A | | 10/1982 | King |
| 4,585,652 A | * | 4/1986 | Miller et al. .............. 604/891.1 |
| 4,969,468 A | | 11/1990 | Byers et al. |
| 5,314,495 A | | 5/1994 | Kovacs |
| 5,361,760 A | | 11/1994 | Normann et al. |
| 5,549,642 A | * | 8/1996 | Min et al. ..................... 607/5 |
| 5,556,421 A | * | 9/1996 | Prutchi et al. ............... 607/36 |
| 5,843,741 A | * | 12/1998 | Wong et al. ............. 435/173.8 |
| 5,919,576 A | * | 7/1999 | Hui et al. .................... 428/545 |
| 6,132,752 A | * | 10/2000 | Pickett et al. .............. 424/423 |
| 6,181,969 B1 | * | 1/2001 | Gord ............................ 607/59 |
| 6,259,937 B1 | * | 7/2001 | Schulman et al. .......... 600/345 |
| 6,266,567 B1 | * | 7/2001 | Ishikawa et al. ............ 607/36 |
| 6,468,304 B1 | * | 10/2002 | Dubois-Rande et al. ... 623/1.42 |
| 2002/0050220 A1 | * | 5/2002 | Schueller et al. ........... 101/486 |
| 2003/0060873 A1 | * | 3/2003 | Gertner et al. ............. 623/1.15 |
| 2003/0077515 A1 | * | 4/2003 | Chen et al. .............. 429/231.8 |
| 2003/0218166 A1 | * | 11/2003 | Tsutsui ........................ 257/40 |

OTHER PUBLICATIONS

Schoenfisch, et al., In Situ Electrochemistry of RU $(NH_3)^{3+}_6$ in a Perfused Heart.

The Electrode—Tissue Interface in Living Heart: Equivalent Circuit as a Function of Surface Area.

* cited by examiner

Primary Examiner—David Zarneke
Assistant Examiner—Igwe U. Anya

(57) ABSTRACT

An implantable electrode and electrode system for contacting living biological material that includes an electrode assembly including at least a portion of the electrode, adapted to contact the living biological material at an electrode/tissue interface, exhibiting conduction that is substantially limited to electron or electron vacancy conduction. The implantable electrode is manufactured by coupling an electrode to a distal end of a conductor, and forming at least one surface of the electrode with a material that conducts electricity in a manner that is substantially limited to electron or electron vacancy conduction when the at least one surface is in contact with the living matter.

11 Claims, 5 Drawing Sheets

TRANSFER FUNCTION H(f) FOR AN Au ELECTRODE IN LIVING PREFUSED HEART. (ATTENUATION [dB] vs. LOGARITHM OF FREQUENCY f [logHz]). NOTE HIGH PASS FILTER BEHAVIOR.

SEMICONDUCTOR AND NON-SEMICONDUCTOR NON-DIFFUSION-GOVERNED BIOELECTRODES

This application claims the benefit of Provisional Application No. 60/328,773, filed Oct. 11, 2001.

BACKGROUND OF THE INVENTION

The use of implantable electrodes has long been known in the medical arts. Electrodes are used, for example, to deliver electrical stimulation to cardiac tissue for pacing, cardioversion, and defibrillation applications. Implanted electrodes are also used to stimulate nerve tissue to modulate cardiac activity, and to treat other cardiovascular disorders. More recently, implanted electrodes have been used to treat incontinence, gastro-intestinal problems, and neurological disorders. Other types of ailments and physiological disorders are treated using similar electrical stimulation.

One problem associated with the use of implanted electrodes to deliver electrical stimulation to living biological tissue involves the accumulation at the electrode/tissue interface of a double layer of charge. More specifically, when an electrode is placed in contact with biological material such as tissue, a layer of electrons accumulates at the conducting surface of the electrode. In response, a corresponding layer of positively-charged ions accumulates within the biological matter near the electrode surface. This double-layer of charge at the molecular level imports a capacitance into the equivalent circuit. This capacitance, sometimes referred to as capacitive impedance, has an effect not unlike an ordinary parallel-plate capacitor, acting as a high-pass filter that distorts signals recorded via the electrode. The impedance minimally affects high-frequency signals, but imposes significant, non-linear attenuation at lower frequencies. Moreover, this capacitance imports a phase shift that varies with frequency. Biological signal recording is significantly impacted since physiological signals include frequency components of 100 Hz or less. Although the foregoing example utilizes a parallel-plate capacitor to illustrate the attenuation imposed at the electrode/tissue interface, this analogy is not entirely accurate. The capacitive impedance Z associated with an ordinary parallel-plate capacitor is inversely proportional to the signal frequency. This relationship can be expressed as $$|Z|=1/(\omega C)$$

wherein $\omega$ is the angular frequency that correlates to signal frequency f via the equation $\omega=2\pi f$. C is a constant referred to as the capacitance, which has a value that is dictated by the geometry, material construction, and potential difference appearing across a given capacitor.

In contradistinction to parallel-plate capacitors, the capacitive impedance at an electrode/tissue interface is inversely proportional to the square root of the signal frequency. This may be expressed as $$|Z|=k(1/\sqrt{\omega})$$

where k is a constant, and $\omega$ is the angular frequency of the signal. This relationship is different from that discussed above with respect to parallel-plate capacitors because of the ionic diffusion that occurs at tissue/electrode interfaces. In other words, the transfer of a signal across an electrode/tissue interface involves the movement of ions within the tissue surrounding the electrode. In contrast to a signal that is transferred across a parallel-plate capacitor via movement of electrons $e^-$ and electron vacancies $h^+$, this ionic movement occurs more slowly, resulting in a larger impedance.

All materials that are currently employed by implantable electrode systems possess a capacitive element such as described above. For instance, all noble metal electrodes and all metal electrodes having a thin passivating film coating, exhibit the type of impedance associated with ionic diffusion. A partial list of such materials includes platinum (Pt), platinum-iridium alloy/s (Pt—Ir), platinized platinum, gold (Au), titanium (Ti), titanium nitride (the nonstoichiometric interstitial nitride of titanium, $TiN_x$ where x varies from 0.8 to 1.15), stainless steel, silver-silver chloride (Ag|AgCl or Ag/AgCl), iridium oxide, alloys of metals of all compositions and components, as well as carbon, glassy carbon and vitreous carbon.

In traditional parallel plate capacitors, capacitive impedance may be decreased by increasing the capacitor surface area. This increased surface area proportionally increases the value of constant C so that the impedance |Z| decreases to zero for a larger and larger surface area. In a similar manner, increasing an electrode surface reduces constant k, reducing the impedance |Z| at the electrode/tissue interface. Although increased electrode area, may reduce impedance, the signal distortion is not completely avoided. Moreover, this increased electrode surface area may be undesirable for several reasons. For example, the increased surface area may result in a lower current density, thereby necessitating the increase of stimulation parameters such as pacing threshold levels, which, in turn, negatively impacts battery life. Moreover, the larger electrode assembly may be more difficult to deliver to a target destination.

The foregoing discussion addresses the problems associated with capacitive impedance at an electrode/tissue interface. In addition to capacitive impedance, other types of galvanic and Faradaic impedances may cause distortion of biological signals measured by implanted electrodes. For example, redox reactions may occur between an electrode surface and ambient chemical species that are not intrinsic to the function of the electrode. These reactions, which may be modeled by amplifiers, diodes, and other non-linear attenuating circuit elements, increase the distortion of recorded signals by importing unpredictable, time-dependent negative impedances.

What is needed, therefore, is an implantable electrode system that provides reduced signal distortion and enhanced signal recovery. Ideally, the resulting electrode/tissue interface is ohmic at physiological frequencies.

DETAILED DESCRIPTION OF THE INVENTION

Figure 1:
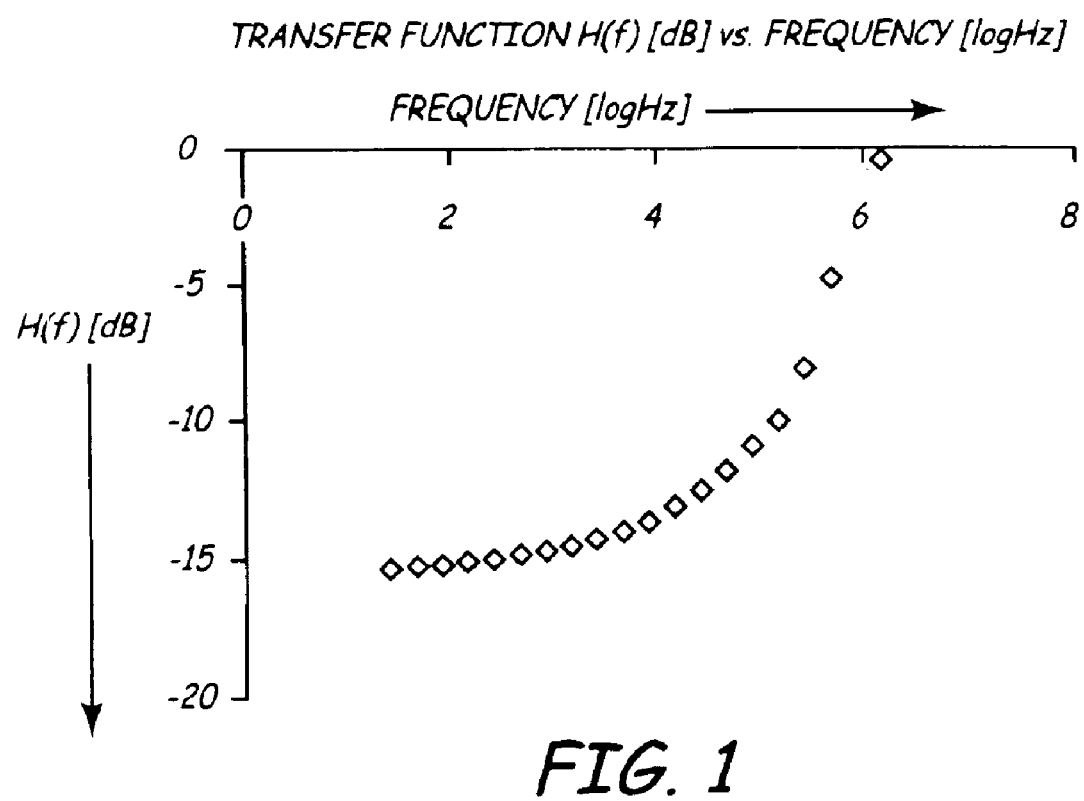
FIG. 1 is a graph illustrating the complex impedance as a function of frequency for an exemplary semiconductor electrode.

The present invention relates to an improved electrode system for reducing distortion of sensed physiological signals. The improved system, which involves the use of a new Halbleiter class of electrodes, differs in certain fundamental characteristics as compared to electrodes of prior art systems. Specifically, within the improved system, conduction at the electrode/tissue interface is characterized by electron $e^-$ or electron vacancy $h^+$ movement rather than the movement of solution phase ions. Thus, the system does not demonstrate diffusional kinetics, and the impedance magnitude is not inversely proportional to the square root of signal frequency. The transfer function within the physiological frequency range of 100 Hz or less is either substantially constant, or mathematically uncomplicated, allowing immediate recording or facile recovery of the source signal. Moreover, the phase shift is substantially constant across this frequency range In one embodiment of the invention, the electrode/tissue interface is substantially ohmic for signals having frequency components of 100 Hz or less. This interface is achieved by providing an electrode formed of a material having semiconductor properties such that electricity is conducted via movement of electrons and holes. Because of these properties, a layer of electrons does not accumulate at the electrode surface. Similarly, a corresponding layer of positively-charged ions does not accumulate within the tissue or other biologic material surrounding the electrode. As a result, the capacitive impedance effects are virtually non-existent, and any remaining signal attenuation is substantially constant in the physiologic frequency band. Moreover, the interface is biologically stable, thereby eliminating galvanic and Faradaic impedances.

Although any material exhibiting semiconductor properties may be used for this purpose, the current embodiment is illustrated with a discussion of an organic conducting polymer electrode. In one embodiment, any sulpher-containing organic compound may be used to coat a conducting material. According to one exemplary embodiment, gold wire may be prepared and cleaned by electrochemical cycling. Alternatively, platinum wire may be cleaned and gold plated. Next, the wire is doped via electrochemical polymerization to form a p-type semiconductor. Anodic potentiostatic pulsing may be performed using a mixture of 3,4-ethlenedioxythiophene (Chemical Abstract Number 126213-50-1, commercially-available from Bayer) and counter ions. An opaque film is created on the wire that may be inspected under a magnifying device such as a Nikkon dissecting microscope to insure that it is free of gross defects. The resulting film-coated wire may serve as a semiconductor polymer film electrode.

In tests conducted with the above-described semiconductor electrode, a heart was exposed and perfused retrogradely with oxygenated buffered balanced salt solutions such as modified Tyrode's solution. A three-electrode potentiostatic configuration was established using a Ag|AgCl reference electrode, a platinum counter electrode, and the exemplary semiconductor electrode. Each of the electrodes was placed within the heart wall in such fashion that its surface was exposed entirely to heart muscle or to nonconductive air. This is the so-called Levy Type-3 insertion method described by Dr. Marc Ovadia in his published work, Schoenfisch M H, Pemberton J E, Ovadia M, Levy M: *Electroanalysis* 1997;9: 135–140 and Ovadia M, Zavitz D H *Electroanalysis* 1998, 10: 262–272, incorporated herein by reference in its entirety.

After the electrode insertion was completed, a specific bias voltage was chosen, and an applied or intrinsic biological signal was recorded. In one instance, an applied sinusoidal signal was recorded and evaluated using an E.G.&G. potentiostat/galvanostat and frequency response analyzer.

FIG. 1 is a graph illustrating the complex impedance for the semiconductor electrode discussed above as a function of frequency. This was used to calculate the attenuation and phase shift for the semiconductor electrode in the living perfused heart.

Figure 2:
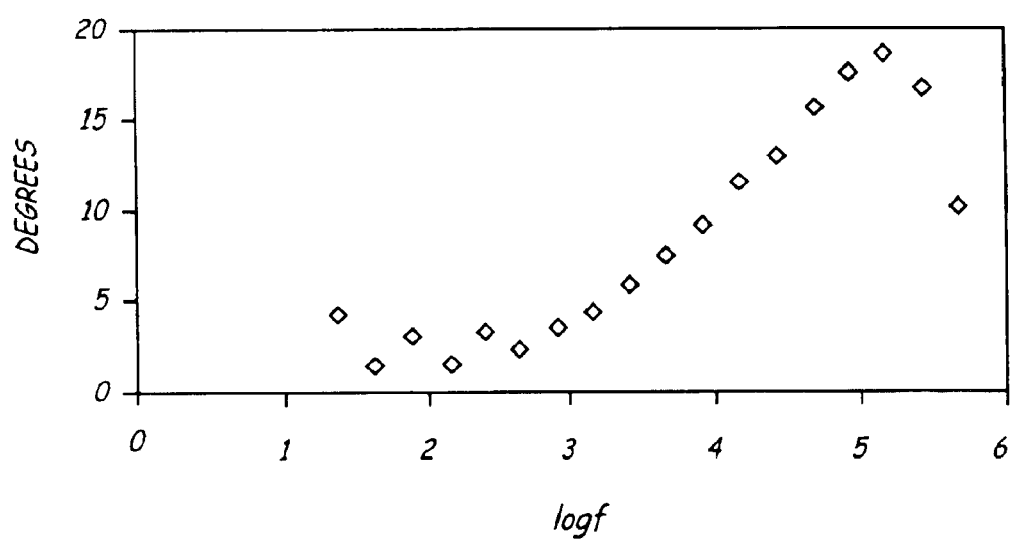
FIG. 2 is a graph illustrating the phase shift for the applied sinusoidal signal in the living heart using an exemplary semiconductor electrode.

FIG. 2 is a graph illustrating the phase shift for the applied sinusoidal signal in the living heart using the semiconductor electrode described above. There is a minimal phase shift constant across the frequency range involving physiologic signals. This may be attributed to charge separation that is similar to a pn junction capacitance or metal|semiconductor interface within the electrode.

Figure 3:
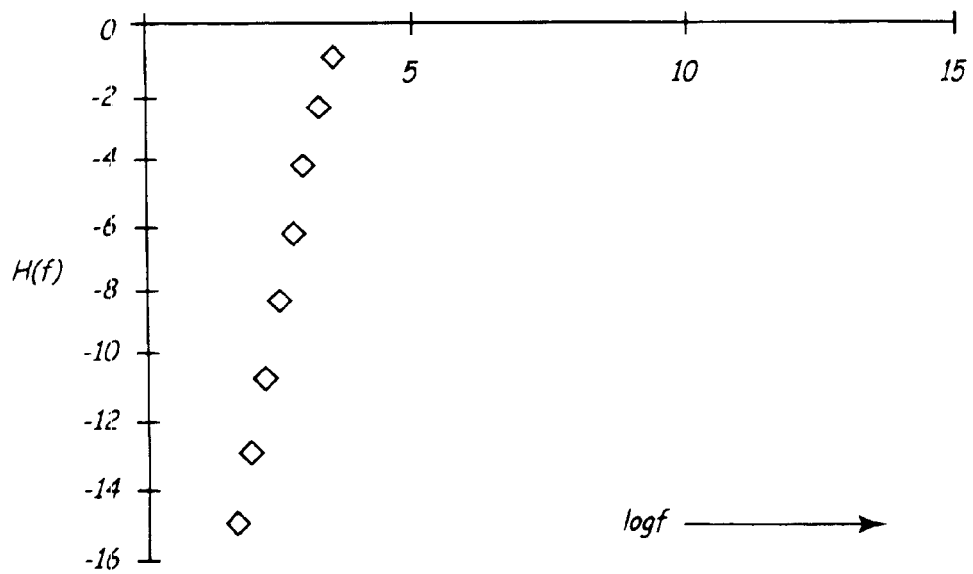
FIG. 3 is a graph illustrating the complex impedance as a function of frequency for an Au noble metal electrode.

FIG. 3 is a graph illustrating the complex impedance for the control electrode as a function of frequency. As discussed above, the control metal electrode is formed of noble metal Au. There is a steep change in the attenuation (differential attenuation) across the physiological frequency range. The behavior depicted here is a best-case scenario for existing technology, having been recorded potentiostatically at a potential free of confounding redox reactions. Despite the fact that this is a best-case scenario, the behavior is very poor, with a source signal that is so distorted as to be irrecoverable.

Figure 4:
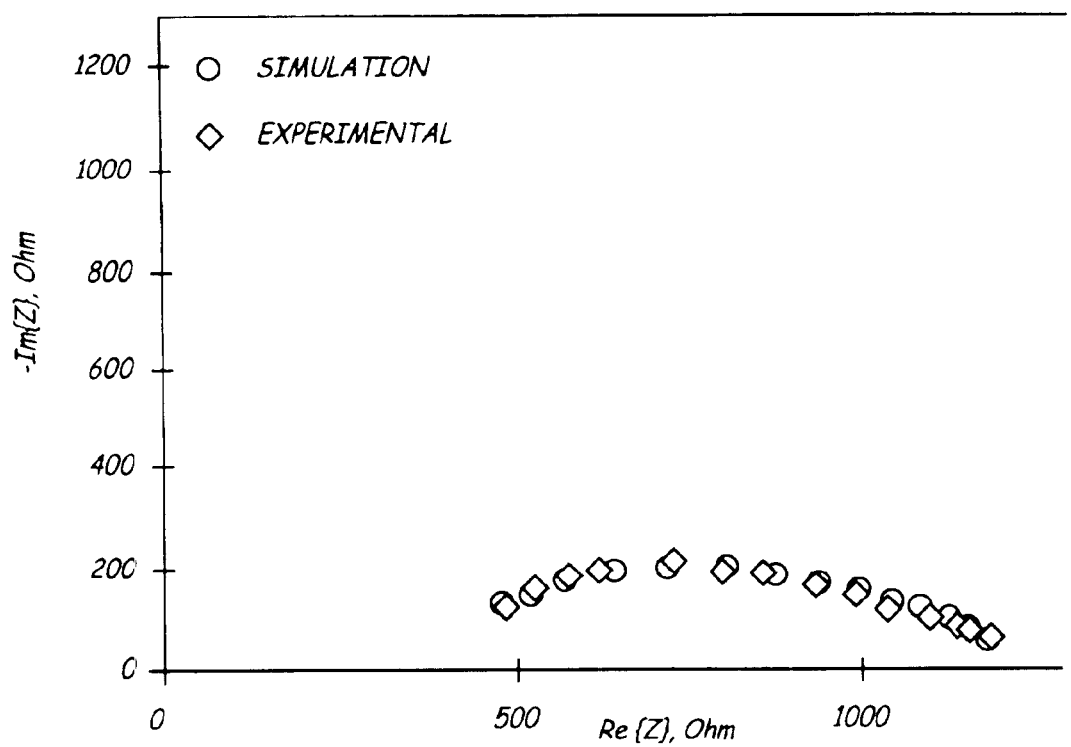
FIG. 4 is a graph illustrating the magnitude and phase of the complex impedance for an exemplary semiconductor electrode.

FIG. 4 is a graph illustrating the magnitude and phase of the complex impedance for the semiconductor electrode. The resistive component of the complex impedance is represented on the real (X) axis, whereas capacitive impedance is represented on the imaginary (Y) axis. The solid data points were obtained experimentally using signal frequencies that extend down to the physiologic frequency range of between 0.5 and 100 Hz. The capacitive impedance component of the complex impedance is shown to be both relatively small, as well as substantially constant. This indicates that virtually no ionic diffusion is occurring at the electrode/tissue interface within the physiologic signal range.

FIG. 4 also includes "open" data points. These data points were derived using the circuit model of FIG. 5. These derived data points correspond closely with the impedance measurements obtained experimentally.

Figure 5:
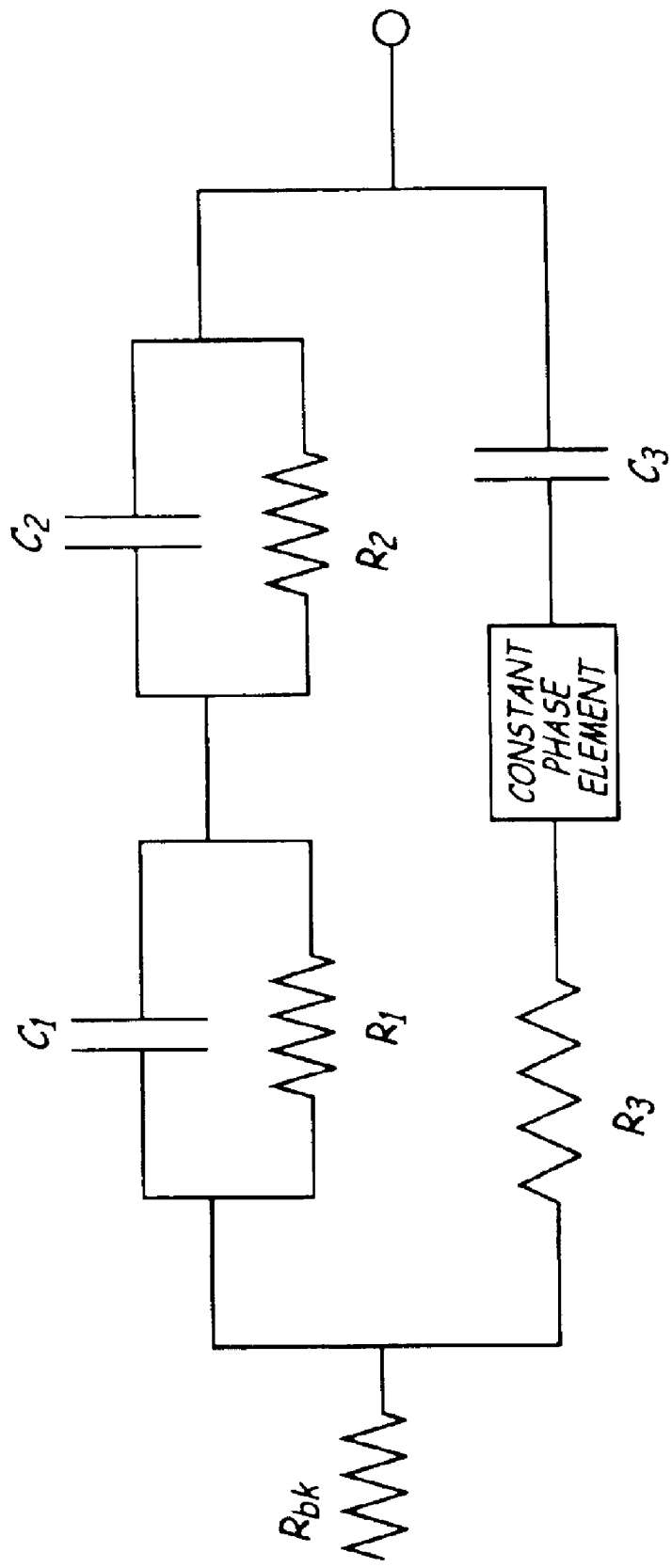
FIG. 5 is a circuit diagram illustrating an equivalent circuit for the semiconductor electrode.

FIG. 5 is a circuit diagram illustrating an equivalent circuit for the semiconductor electrode. As stated above, the validity of this model is substantiated by the close correspondence between the derived and experimental data points of FIG. 4. As may be appreciated by those skilled in the art, when a low frequency signal is applied across the terminals of the circuit, the impedance approaches a resistance comprising the sum of resistors $R_b$, $R_1$, and $R_2$, thus illustrating the minimization of the capacitive impedance component in the physiological signal range.

Alternative Embodiments

Although the foregoing description discusses a gold electrode doped to form a p-type semiconductor, any electrode formed of a material possessing demonstrable electron or electron vacancy conduction at the electrode/tissue interface may be utilized in the current invention. This includes almost all semiconductor electrodes of all classes that are formed using all currently-known, or yet-undeveloped, methods of preparation. More specifically, any solid and thin-film n-type and p-type semiconductor that is formed using any suitable preparation technique may be employed in the current invention. This encompasses, for example, all semiconductor electrodes of polythiophene, derivatized polythiophene, polyNmethylpyrrole, poly3methylthiothene, polyaniline, and conjugated polymer classes, including those prepared using doping or other preparation aspects that improve or deteriorate conductivity to metal, semimetal or insulator levels. One semiconductor material that is a known exception to the foregoing generalization is the mixed charge-carrier material Ag|AgCl. This material has known semiconductor properties that are not demonstrable in biological systems, making it unsuitable for use in the current application.

While the above discussion focuses on the use of electrodes formed of materials exhibiting semiconductor properties, the current invention further includes other types of electrodes that eliminate ionic conduction within the physiologic signal range. For example, it is possible to form an electrode by coating a conductive material such as gold with a very thin layer of virtually any non-conducting material. This thin layer of non-conducting material need only be one molecule deep. In one embodiment, the non-conducting material is a self-assembled monolayer (SAM) of any organic species that possesses a thiol functionality, such as n-alkylthiol. The SAM may be formed on any biocompatible conductive material, such as a gold conductive element. So long as this non-conductive layer does not include imperfections, ionic conduction is prevented at the electrode/tissue interface.

The impedance of an electrode possessing a thin coating of non-conducting material at its outer surface is similar to that of a parallel-plate capacitor. That is, the impedance is inversely proportional to signal frequency. As discussed above, this is in contrast to impedance associated with ionic conduction, which is inversely proportional to the square root of signal frequency. While not as desirable as the previously-discussed embodiment involving semiconductor electrodes exhibiting ohmic characteristics at lower frequencies, this alternative embodiment is never-the-less an improvement over prior art electrode systems. This alternative embodiment includes all electrodes formed of any material whatsoever that may be covered by a thin or thick film of substances designed to confer the properties involving electron or electron vacancy conduction on the aggregate electrode. This may include capacitive or insulating electrodes.

It may be noted that any of the embodiments discussed above are suitable for use in all potentiostatic, voltage, or current-measurement applications associated with biological signals. It may further be noted that any of the foregoing electrode systems may be modified to form patch-clamp, microelectrode or ultra-microelectrode systems. Such systems, which have traditionally been formed using glass or quartz micropipettes, are sized so that recordation of signals at the cellular level is possible. These types of electrodes are suited for use in biophysical recordings or microelectrochemical measurement applications. Such applications include whole-cell-intracellular recording, or routine microelectrode intracellular recording amperometry and voltammetry with microelectrodes or ultra-microelectrodes in living systems. More specifically, the current invention is suitable for use in all of the applications customarily employing Ag|AgCl electrodes.

While a particular embodiment of the present invention has been shown and described, modifications may be made. It is therefore intended in the appended claims to cover all such changes and modifications, which fall within the true spirit and scope of the invention.

What is claimed is:

1. An implantable electrode system for contacting living biological material and sensing electrical potential in the biological material, comprising:

an electrode assembly including at least a first portion adapted to contact the living biological material at an electrode/tissue interface, the first portion of the electrode assembly exhibiting conduction that is substantially limited to electron or electron vacancy conduction during sensing of the electrical potential in the biological material, wherein the first portion is formed of a material exhibiting semiconductor properties.

2. The electrode system of claim 1, wherein the first portion is formed of a material selected from the group consisting of polythiophene, derivatized polythiophene, and conjugated polymer classes.

3. The electrode system of claim 1, wherein the first portion includes a material doped to form a p-type semiconductor.

4. The electrode system of claim 3, wherein the first portion includes a gold portion having at least one surface in proximity to the doped material.

5. The electrode system of claim 1 wherein the doped material is doped via electrochemical polymerization to form a p-type semiconductor.

6. The electrode system of claim 5, wherein the electrochemical polymerization includes performing anodic potentiostatic pulsation using a mixture of 3,4-ethlenedioxythiophene and counter ions.

7. An implantable electrode, comprising:

a conductor; and an electrode assembly coupled to the conductor, the electrode assembly have at least one portion adapted to contact living biological material and that demonstrates semiconductor properties when in contact with the living biological material to sense electrical properties in the biological material, wherein the at least one portion performs conduction solely via electron or hole conduction when in contact with the living biological material, wherein the at least one portion includes a doped material doped to form a p-type semiconductor.

8. The electrode of claim 7, wherein the at least one portion is formed of a material selected from the group consisting of polythiophene, derivatized polythiophene, and conjugated polymer classes.

9. The electrode of claim 7, wherein the first portion includes a gold portion having at least one surface in proximity to the doped material.

10. The electrode of claim 9, wherein the doped material is doped via electrochemical polymerization to form the p-type semiconductor.

11. The electrode of claim 10, in the electrochemical polymerization includes performing anodic potentiostatic pulsation using a mixture of 3,4-ethlenedioxythiophene and counter ions.

* * * * *